United States Patent [19]

Tice et al.

[11] Patent Number: 4,835,139
[45] Date of Patent: May 30, 1989

[54] PROCESS FOR INCREASING THE ANTAGONISTIC EFFECT OF PEPTIDIC COMPOUNDS ON HORMONE-DEPENDENT DISEASES

[75] Inventors: Thomas R. Tice, Birmingham, Ala.; Piero Orsolini, Martigny, Switzerland; Andrew V. Schally, New Orleans, La.

[73] Assignee: Debiopharm S.A., Lausanne, Switzerland

[21] Appl. No.: 52,319

[22] Filed: May 19, 1987

Related U.S. Application Data

[63] Continuation-in-part of Ser. No. 652,043, Sep. 19, 1984, abandoned.

[30] Foreign Application Priority Data

Sep. 23, 1983 [CH] Switzerland ............................ 5187/83

[51] Int. Cl.$^4$ .............................................. A61K 37/43
[52] U.S. Cl. ........................................ 514/15; 514/800
[58] Field of Search .................................. 514/16, 800

[56] References Cited

U.S. PATENT DOCUMENTS

| 3,773,919 | 10/1970 | Boswell et al. | 424/486 |
|---|---|---|---|
| 3,835,108 | 2/1972 | Imner et al. | 530/313 |
| 3,887,699 | 6/1975 | Yolles | 424/19 |
| 4,010,125 | 6/1975 | Schally et al. | 530/313 |
| 4,018,726 | 4/1977 | Schally et al. | 260/8 |
| 4,024,121 | 5/1977 | Schally et al. | 260/112.5 LA |
| 4,234,571 | 11/1980 | Nestor et al. | 424/177 |
| 4,585,651 | 4/1986 | Beck et al. | 424/88 |
| 4,675,189 | 6/1987 | Kent et al. | 424/490 |

FOREIGN PATENT DOCUMENTS

| 21234 | 1/1981 | European Pat. Off. . |
|---|---|---|
| 52510 | 5/1982 | European Pat. Off. . |
| 58481 | 8/1982 | European Pat. Off. . |
| 7038364 | 10/1970 | France . |
| 0615662 | 6/1976 | Switzerland . |
| 2034182 | 10/1979 | United Kingdom . |

OTHER PUBLICATIONS

Chang, J. Biseng., vol. 1, pp. 25–32, 1976.
Clayton, J. Endoc. vol. 111, pp. 152–161, 1981.
Nestor, "Long Acting LHRH Agonists and Antagonists" (1984).
Sanders, "An Injectable Biodegradable Controlled Release Delivery System for Nafarelin Acetate" (1984).
J. Pharma. Sci., vol. 59, No. 10, p. 1373, Oct. 1970.
(List continued on next page.)

Primary Examiner—Delbert R. Phillips
Attorney, Agent, or Firm—Pennie & Edmonds

[57] ABSTRACT

The antagonistic effect of the releasing hormone of LH and FSH or of one of its synthetic analogues selected from the group (pyro)Glu-His-Trp-Ser-Tyr-D-Trp-Leu-Arg-Pro-Gly-NH$_2$ (pyro)Glu-His-Trp-Ser-Tyr-D-Phe-Leu-Arg-Pro-Gly-NH$_2$ and (pyro)Glu-His-Trp-D-Ser-Tyr-D-Leu-Leu-Arg-Pro-NHR$^1$ ($R^1$ being an alkyl group). On hormone-dependent diseases can be increased by coating such compounds by micro-encapsulation or by matrix formation with a copolymer of a lactide and a glycolide. The initial stimulating effect of the above-mentioned compounds is increased by this coating, with about 23 to 50% of the active principle of the analog being released within about 1–5 days after injection to a human, with the remainder released over a period of between about 3 weeks and two months.

27 Claims, 2 Drawing Sheets

OTHER PUBLICATIONS

"Controlled Release of Biologically Active Agents", Tanquary A. C., Lacey R. E., editors, Plenum Press, New York, 1974.

"Polymeric Delivery Systems", Kostelnik R. J. ed., Midl. Macromol. Monogr., vol. 5, 1978.

"Sustained and Controlled Release Drug Delivery Systems", Robinson J. R. ed., Marcel Dekker, New York, 1979.

"Controlled Release of Bioactive Materials", Baker R. ed., Academic Press, New York, 1980.

"Controlled Release of Macromolecules", Chemtech, pp. 98-105, Feb. 1982.

European Patent Office's letter dated Oct. 24th, 1983, Ref. IMA/22210.

U.S. Patent 3,773,919, filed Oct. 8th, 1970, published Nov. 20th, 1973, (E. I. DuPont de Nemours, U.S.A.), G. A. Boswell and R. M. Scribner, Inventors.

"Biodegradable Semipermeable Microcapsules Containing Enzymes, Hormones, Vaccines, and other Biologicals", Thomas M. S. Chang—Journ. Bioengineering, vol. 1, pp. 25-32, 1976.

"Sustained Release Microcapsules and Microparticles of Polylactide Polymer", Yolles et al., J. Pharma. Sci., vol. 64, p. 348, 1975.

"New Long-Acting injectable Microcapsule Contraceptive System", Lee R. Beck et al., Am. J. Obstet. Gynecol., vol. 135, No. 3, pp. 419-426, Oct. 1979.

"A New Long-Acting Injectable Microcapsule System for the Administration of Progesterone", Lee R. Beck et al., Fertility and Sterility, vol. 31, No. 5, pp. 545-551, May 1979.

"Long-Acting Steroidal Contraceptive Systems", Lee R. Beck et al., Research Frontiers in Fertility Regulation, vol. 1, No. 1, Jul. 1980.

"Sustained Release of Antibiotics from Biodegradable Microcapsules", D. H. Lewis et al. (SRI), 7th International Symposium on Controlled Release of Bioactive Materials, Ft. Lauderdale, Fla., Jul. 28-30th, 1980.

"Lactic/Glycolic Acid Polymers", Donald L. Wise et al., Drug Carriers in Biology and Medicine, Gregory Gregoriadis ed., Academic Press-New York, pp. 237-270, 1979.

Applicants letter (Mewburn Ellis & Co., Authorized Representative), dated Apr. 27th, 1986.

U.S. Patent 4,010,125, filed Jun. 12th, 1975, published Mar. 1st, 1977.

U.S. Patent 3,835,108, filed on Feb. 15th, 1972, published Sep. 10th, 1974.

(a) "Microencapsulation of the Peptide Nafarelin Acetate for Controlled Release", John S. Kent et al., Long-Acting Contraceptive Delivery Systems, Zatuchni et al. ed., Harper & Row-Philadelphia, pp. 169-179, 1983.

(b) "Comparisons of the Potential Utility of LHRH Agonists and Antagonists for Fertility Control", Brian H. Vickery.

(c) "Controlled Delivery of an LHRH Analogue from Biodegradable Injectable Microspheres", Lynda M. Sanders et al., Journal of Controlled Release, vol. 2, pp. 187-195, 1985.

(d) "An injectable Biodegradable Controlled Release Delivery System For Nafarelin Acetate", L. M. Sanders et al., in LHRH and its analogues, Labrie, Belanger and Dupont Eds., pp. 53-62, 1984.

"Radioimmunoassay of (D-Trp6)-Luteinizing Hormone-Releasing Hormone: Its Application to Animal Pharmacokinetic Studies after Single Injection and Long-Acting Formulation Administration", Eric Ezan et al., Regulatory Peptides, vol. 14, pp. 155-167, 1986.

"Inhibition of Prostate Tumors by Agonistic and Antagonistic Analogs of LH-RH", A. V. Schally et al. The Prostate, vol. 4, pp. 545-552, 1983.

"Current Status of Antagonistic Analogs of LH-RH as a Contraceptive Method in the Female", A. V. Schally et al., Research Frontiers in Fertility Regulation, vol. 2, No. 5, Jul. 1983.

"Long-Acting Delivery Systems for Peptides: Inhibition of Rat Prostate Tumors by Controlled Release of (D-Trp6)-Luteinizing Hormone-Releasing Hormone from Injectable Microcapsules", A. V. Schally et al., Proc. Natl. Acad. Sci., vol. 81, pp. 5845-5848, Sep. 1984.

"Prolonged Controlled-Release of Nafarelin, a Luteinizing Hormone-Releasing Hormone Analogue, from Biodegradable Polymeric Implants: Influence of Composition and Molecular Weight of Polymer", L. M. Sanders et al., J. Pharm. Sci., vol. 75, No. 4, pp. 356-360, Apr. 1986.

PROCESS FOR INCREASING THE ANTAGONISTIC EFFECT OF PEPTIDIC COMPOUNDS ON HORMONE-DEPENDENT DISEASES

CROSS REFERENCE TO RELATED APPLICATIONS

This application is a continuation-in-part of application Ser. No. 652,043, filed Sept. 19, 1984, abandoned.

TECHNICAL FIELD

The invention is concerned generally with the field of pharmacology and clinical medicine, and more particularly relates to a process for significantly increasing the antagonistic and paradoxical effect of certain compounds with a peptidic structure on hormone-dependent diseases.

SUMMARY OF THE INVENTION

This invention relates to a sterilized sustained release pharmacological formulation comprising a LH-RH analog and a polylactide-glycolide copolymer which releases between about 20 and 55% of the analog within the first five days after administration to a human, with the remainder of the analog being released within about 3 weeks to 2 months thereafter.

Another embodiment of the invention is directed to a process for increasing the paradoxical and antagonistic effect of the releasing hormone of a LH-RH analog on hormone dependent diseases in a human, characterized in that a therapeuticaly effective amount of one of the pharmacological formulations of the invention is administered to the human, preferably by intramuscular injection. This process stimulates LH and FSH in the human for the first few days, followed by a substantial and almost complete suppression of LH and FSH thereafter for at least 3 weeks to as long as 2 months.

DETAILED DESCRIPTION OF THE INVENTION

One object of the invention is a process for increasing the antagonistic effect of the releasing hormone of LH and FSH or of one of its synthetic analogues on hormone-dependent diseases characterized in that these compounds are formulated with a copolymer of D,L-lactide and glycolide so that, when the compounds are injected into a patient, about 20 to 50 percent of the active principle is released with the first five days after the injection.

Yet another object of the invention is a process for decreasing the initial stimulation of the releasing hormone of LH and FSH or of one of its synthetic analogues characterized in that said compounds are microencapsulated by means of a copolymer of D,L-lactide and glycolide. The invention is further defined in the Claims.

The releasing hormone of LH and FSH is a decapeptide of the following structure:

(pyro)
Glu-His-Trp-Ser-Tyr-Gly-Leu-Arg-Pro-Gly-NH$_2$.

This hormone and its synthetic analogs exert an antagonistic effect on a number of biological processes which are specific to mammals, and has been therefore suggested—among other uses—as an ovulation regulating agent. In human medicine, such compounds are advantageously used for the treatment of certain endocrine disorders, such as for example those of the menstrual cycle, or for contraceptive purposes (for example, see Swiss Patent No. 615,662 on this subject).

Whether the hormone-dependent biological processes be of a pathological or a natural origin, it is desirable in certain instances to administer the above-mentioned compounds in a continuous manner over prolonged periods and preferably as preparations with an activity extending in time, for example through controlled release or the formation of deposits. Such formulations are known and widely used in various areas of medicine, and can consist, for example of a salt with a low degree of solubility in the body fluids or of a highly viscous liquid. Recently, the use of bio-compatible polymers, such as the copolymer of D,L-lactide and glycolide has been proposed for this purpose: it has been possible to obtain with such material matrixes which can trap the pharmacologically active ingredient to release it in a controlled manner (see for example the European Patent Application No. 0058481). The use of a copolymer such as D,L-lactide and glycolide has also been suggested for the coating of LH-RH and some of its analogues in the preparation of microcapsules (see for example the European Patent Application No. 0052510). From these disclosures, medical preparations are thus obtained which exhibit a delayed release of the active principle against various hormone-dependent diseases.

Independently from what precedes, it has been recently proposed to use the LH-RH or some of its synthetic analogues for the treatment of hormone-dependent diseases on which these compounds exert a paradoxical and antagonistic effect (see for example A. V. Schally et al. in "Frontiers of Medicine—Implications for the Future", Human Science Press, N.Y. 1983 : Biomed. Pharmacoether. 36 No. 2, 120 1982). Among such diseases, one can mention for example breast cancer, prostate cancer, endometriosis or benign prostatic hyperplasia. For such treatments, it has been found desirable to improve the conditions under which these compounds are administered to take into account the sometimes undesirable side-effects of LH-RH and of its synthetic analogs: in fact, it is for example known that such compounds raise initially the testosterone level, which is contrary to the desired therapeutic action. The physician when facing such a problem does not have at present the possibility of administrating compounds with antagonistic properties in sufficiently high doses without causing undesirable side-effects, such as pain.

The merit of the applicants' parent application is to provide a new and original solution to overcome the above-described problem. Thanks to the object of this invention, it is now possible to administer preparations, which although containing an identical dose of pharmacologically active ingredient (LH-RH or synthetic analogs) demonstrate an antagonistic effect notably better than that obtained with the same ingredient administered as a non-encapsulated or non-coated preparation. Such an effect, which can be described as synergetic, is totally unexpected from the present knowledge of the art. Moreover, such an effect is advantageously accompanied by a simultaneous decrease of the initial stimulating effect which is inherent to these compounds.

The objective of the present invention is to provide a sustained release formulation comprising LH-RH or a LH-RH analog and a polyactide-glycolide copolymer wherein between about 20 and 55% preferably between 23 and 50% of the active principle of the analog is released within the first five days after administration to a human, with the remainder of the analog being released within about 3 to 6 weeks thereafter.

A preferred way of achieving this objective is by proceeding to the coating or encapsulation of the LH-RH analogs with a copolymer of D,L-lactide and glycolide. Such a copolymer is generally known (see references), and can be produced of the quality required for the present invention according to known practices. According to the invention, however, properties of the copolymer are specifically defined to achieve the desired results. The molar proportion of D,L-lactide and of glycolide in the copolymer is preferably situated between approximately 50:50 and 55:45, while the copolymer preferably has an average molecular weight ($M_w$) situated between approximately 30,000 and 100,000, and preferably between approximately 36,000 and 50,000, to which corresponds a viscosity situated between approximately 0.5 and 0.8, preferably 0.5 to 0.7 dl/g. By coating micro-particles according to usual practices with copolymers such as those defined above, a high degree of coating is achieved which amounts to approximately 70 to 90%, depending on the specific processing conditions utilized.

In this manner, the shape and the size of the microcapsules are easily controlled, and also the proportion of pharmacologically active ingredients can be accurately controlled. Generally, the particle size is less than 250 microns. To achieve the desired effect according to the invention, spherical microparticles are used which have a diameter preferably situated between approximately 30 and approximately 50 microns and which contain between approximately 1.5 and 3, preferably 1.7 and 2.9% (w/w) of coated active ingredient. Details of typical values for the microparticles obtained according to the present invention are given in the examples.

Microparticles having the characteristics given above provide a product capable of releasing in vivo or in similar conditions the active ingredient over a period of approximately 25 to 30 days from a single administered dose. The process of the invention has also the advantage that the microparticles can be coated in almost sterile conditions, because the encapsulation is carried out in a substantially organic medium and the peptide to be encapsulated is dissolved in sterile water or added in a dry state. However, for administration to humans, the coated microparticles are preferably sterilized by irradiating with gamma rays: it has been observed that this sterilization method does not alter the properties of the product provided that this is accomplished by exposure to gamma rays at a dosage of between 2.5 and 2.8 Megarads. Further, such microparticles can be kept under the usual conditions of storage of similar medicines for example from 4 to 6 months at approximately 4° to 21° C.

It is also possible to form a matrix compound of the analog and copolymer wherein the matric compound is capable of releasing the desired amounts of active principle in vivo. Those skilled in the art are capable of varying the amount and properties of the copolymer used in the matrix to achieve the desired release characteristics.

Any of the LH-RH analogs disclosed in EP 0,052,510 are suitable for use in the present invention in the form of matrix or encapsulated compounds, but the most advantageous formulations are the LH-RH analogs given below which are encapsulated with a copolymer of D,L-lactide and glycolide in the manner described herein:

(pyro)
Glu-His-Trp-Ser-Tyr-D-Trp-Leu-Arg-Pro-Gly-NH$_2$, (pyro)
Glu-His-Trp-Ser-Tyr-D-Phe-Leu-Arg-Pro-Gly-NH$_2$, or (pyro)
Glu-His-Trp-D-Ser-Tyr-D-Leu-Arg-Pro-Gly-NH R$^1$, wherein R$^1$ is an alkyl group.

To obtain the desired antagonistic effect, the microcapsules are preferably administered as injectable suspensions. The size of the particles (preferably 30 to 50 microns) obtained according to the process of the invention is such that their injection offers no difficulty. The biocompatible diluents used for this purpose are known in the art. The injection is generally given by the intra-muscular route. The amount thus injected depends to a considerable extent on the disease which is treated, on the part of the body which is treated, and on the general state of the patient. Expressed in weight of pharmacologically active ingredient (or peptide), the dose injected can advantageously be determined as between 0.1 and 10 micrograms per day per kilogram of body weight (these doses are expressed in weight of pharmacologically active ingredient released from one single initial administered dose of the encapsulated product). Different comparative tests carried out in appropriate conditions showed that at the same daily levels of administration of the active ingredient, the therapeutical effect of the encapsulated preparation was significantly higher. The same observation was made when the dose of active ingredient which had been encapsulated was lower by 50% than the dose of non-encapsulated active ingredient.

When comparative tests were carried out in vivo with rats for example, it was found that the administration of the same doses of the pharmacologically active ingredient (peptide) resulted in a decrease of the weight of a prostatic tumor of approximately 27% in the case of the non-encapsulated compound and of approximately 80% in the case of the compound encapsulated, according to the invention. Moreover, a decrease of approximately 80% was recorded in the testosterone level of the rats receiving the encapsulated compound.

The invention will be further illustrated in a more detailed manner with the following examples.

EXAMPLE 1

Encapsulation of a Decapeptide

The various operations for preparing a pharmacologically active preparation were carried out with the compound of the following formula (compound A):

(pyro)
Glu-His-Trp-Ser-Tyr-D-Trp-Leu-Arg-Pro-Gly-NH$_2$

This compound was obtained according to the process described for example in the Swiss Patent No.

615,662. The peptide content of the preparation was approximately of 80% (w/w).

Encapsulation

A copolymer of D,L-lactide and glycolide with a 50/50 molar ratio of D,L-lactide to glycolide and with an average molecular weight of 53,000 is first dissolved in an appropriate organic phase and the solution is introduced into a reaction vessel provided with an agitator. A separate solution of compound A in sterile water is prepared. This solution is poured slowly into the vessel while stirring the mixture with the agitator rotating at approximately 2,000 rpm. Alternately, it is possible to add Compound A as a dry solid, rather than as a solution. A phase separation inducer is added to the mixture under agitation to cause the coacervation of the poly-(D,L-lactide-co-glycolide) and the coating of compound A. The mixture now containing the embryonic microcapsules is next poured into a hardening liquid under agitation, which continues for 30 minutes at approximately 800 rpm. After filtration, the product is dried under reduced pressure for 24 hours.

The product was obtained by this procedure with a yield amounting to 76% of the theoretical yield.

Characterization

Spherical particles having a diameter in the range from 30 to 50 microns (the measurements were made on photographs taken with a scanning electron microscope).

Content of encapsulated compound, 2.07% (w/w). The efficiency of the encapsulation was of 70%. To determine the content of encapsulated compound, the microparticles are dissolved in methylene chloride, the methylene chloride solution is extracted with a pH 7.4 phosphate buffer, and the amount of decapeptide measured by High Pressure Liquid Chromatography.

The microparticles obtained according to this method can be when desired irradiated with gamma rays at about 2.5 Mrad before being administered in vivo. before being administered in vivo.

EXAMPLE 2

By varying the conditions under which the encapsulation of compound A described in Example 1 was performed, we obtained the results shown in Table 1. The compound A which was used had a peptide content of about 80% (w/w). Table 1 gives the physical characteristics of the preparation thus obtained. The various preparations of microparticles were tested for the release of Compound A into a 0.01 molar aqueous solution of monosodium phosphate pH 7.4 at 37° C.

EXAMPLE 3

The antagonistic effect of the encapsulated compound A (see the previous examples) and of the non-encapsulated compound A was studied on rats having the prostatic tumor R-3327-H according to Dunning. (DUNNING R-3327-H PROSTRATE CARCINOMA).

In vivo tests were carried out on groups of 7 to 10 animals during a period of 30 days.

The administration of the non-encapsulated Compound A adequately dissolved in a biocompatible solvent was achieved by the subcutaneous injection of two doses every day, each dose containing 25 micrograms of compound A (Table 2) or 12.5 micrograms of compound A (Table 3).

The administration of the encapsulated compound A was achieved by the daily intra-muscular injection of doses of the preparation suspended in a biocompatible solvent, each such dose containing 25 micrograms of compound A.

The results of the observation which were made are given in Tables 2 and 3. The evolution of testosterone was measured during 30 day period for those animals receiving the daily dose of 25 micrograms of compound A. FIG. 1 clearly illustrates the enhanced antagonistic effect (i.e. the decrease of the testosterone blood content) of the compound A when encapsulated.

_____: Administration of non-encapsulated compound A

_ _ _ _ _ _ _ _ _ _: Administration of encapsulated compound A.

EXAMPLE 4

The inhibition of the initial stimulatory effects of compound A was tested in vivo with two separate groups including 5 patients each. The hormones which were determined were:

_____: testosterone (in ng/ml)

_ _ _ _ _ _ _ _ _ _: LH (in mIU/ml)

— — . — . — . —: FSH (in mIU/ml)

FIG. 3 shows clearly the total absence of the initial stimulatory effect on the testosterone level.

EXAMPLE 5

Compound A was encapsulated with a copolymer of D,L-lactide and glycolide having a molecular weight of 39,127 daltons, a molar ratio of lactide to glycolide of 52:48 and a viscosity of 0.65.

Figure 1:
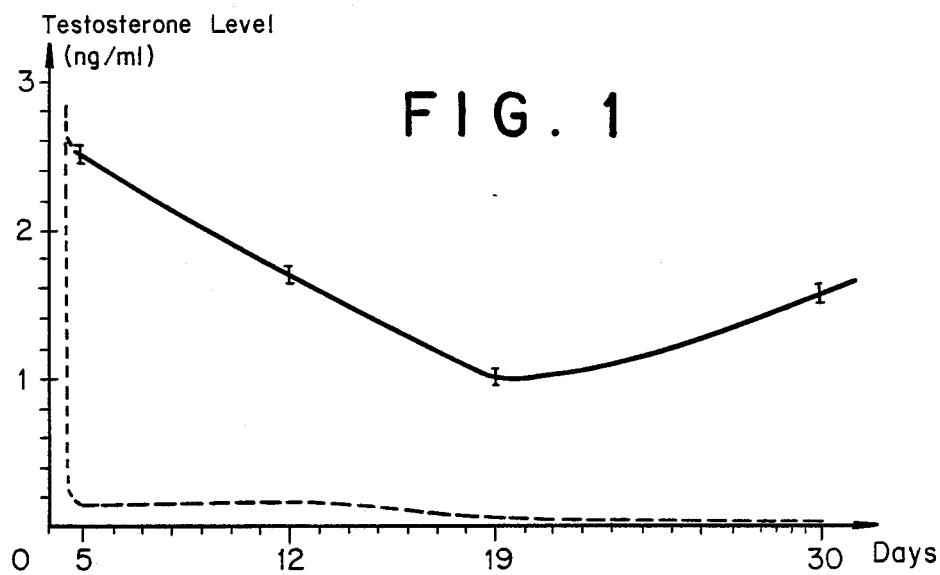
Figure 2:
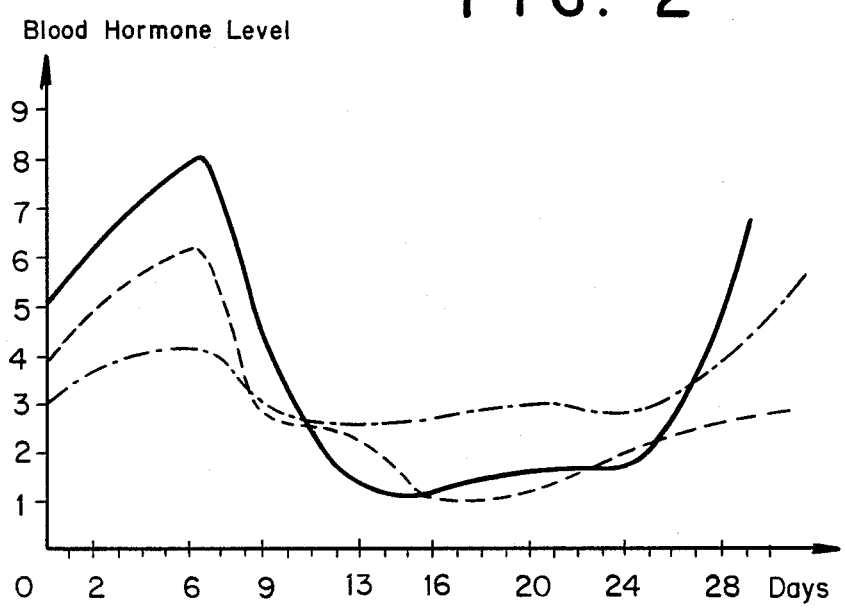
FIG. 2 shows the results obtained with the first group of patients treated with one daily dose of 100 gamma of non-encapsulated compound A during 5 days, and thereafter with one daily dose of about 100 gamma of encapsulated compound A.
Figure 3:
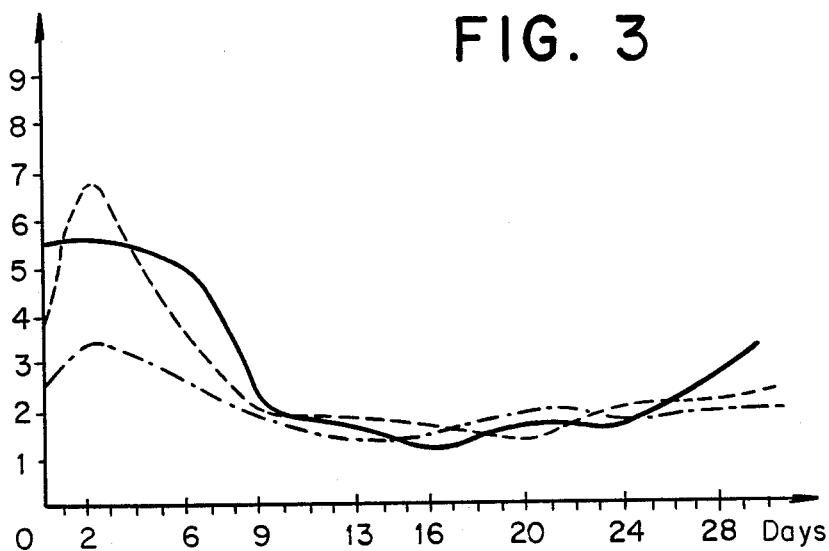
FIG. 3 shows the results obtained with the second group of patients treated with one monthly injection which is equivalent to a daily dose of 100 gamma of encapsulated compound A.
Figure 4:
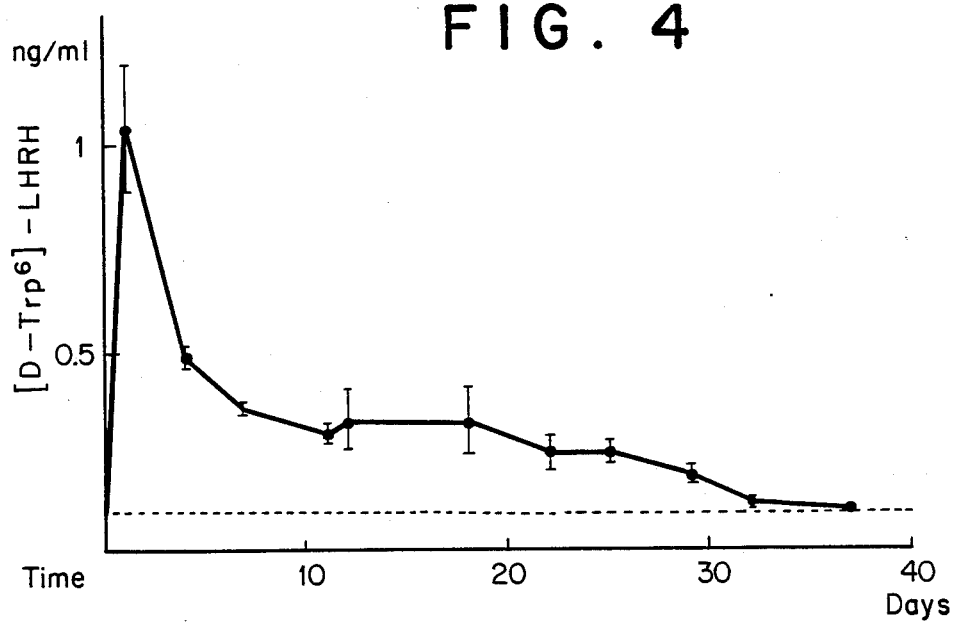

3 mg of this encapsulated compound in suspension was injected intramuscularly into dogs to assess the delivery of the active ingredient over time. FIG. 4 shows the release pattern of the active principle, wherein a rapid release of the peptide was found at day 1 followed by a plateau between day 4 and 31, the broken line representing the basal level of the decapeptide-like immunoreactivity in dog plasma before injection. Stimulation of gonadotropin cells led to a rise in testosterone plasma concentration at one day, but castration level was obtained between day 4 and day 7 and maintained until day 30.

EXAMPLE 6

Three encapsulated compound A formulations (F1, F2, F3) were administered to beagle dogs by intramuscular injection to determine the release of active principle over time with once a month dosing. Additionally, the relative bioequivalence of the three formulations was examined as reflected by plasma concentrations of the active principle and by their ability to reduce plasma testosterone. Statistically significant differences in the total amount of drug released from the formulations were not present. However, the course of release of the active principle was different, as was the profile of testosterone suppression, for the different formulations.

F1 and F3 demonstrated similar patterns of release of the active principle and testosterone suppressions. Both released approximately 50% of their total by day 1 and demonstrated peak plasma concentrations at the first (2 hour) sampling time. F2 released less decapeptide on day 1 (23% of total released) and also had lower peak plasma concentrations than the other formulations. Testosterone concentration profiles showed an initial elevation, lasting for 1–5 days (greatest in F2), followed by depression and total suppression lasting from 30 to 60 days postdose (greatest in F1 and F3). A positive correlation was established between the amount of decapeptide released on day 1 and testosterone suppression. The cessation of testosterone suppression was associated with the lack of detectable decapeptide concentrations.

These results surprisingly demonstrate that the greatest release of the active principle within the first 5 days after injection, preferably within the first 3 days and most preferably, by day 1, provides the best therapeutic activity, with a short initial stimulation phase of the hormone in the body, followed by a depression and total suppression for a period of between about 3 and 6 weeks to 2 months, usually for at least about 25–30 days. It is believed that the initial release of a substantial amount of the analog produces the greater and more rapid suppression that is observed. One reason for the increased initial release of the active principle is believed to be the low hydrophobic character of coatings formed on the LH-RH compound as described above, which enables the resulting compositions to be more soluble in the body fluids. Also, since the initial stimulation is short, higher amounts of the active principle can be used with a lesser painful reaction in the patient.

While it is apparent that the invention herein disclosed in well calculated to fulfill the desired results, it will be appreciated that numerous modifications and embodiments may be devised by those skilled in the art such as, for instance, those claimed in U.S. Pat. Nos. 3,887,699 and 3,976,071, and it is intended that the appended claims cover all such modifications and embodiments as fall within a the true spirit and scope of the present invention.

TABLE NO. 1

| Test No. | Copolymer (g)* | $CH_2Cl_2$ (g) | Comp. A (mg) | Silicone oil[1] (ml) | Speed (rpm) | Yield (%) |
|---|---|---|---|---|---|---|
| 1 | 2.00 | 122.0 | 105.7 | 60 | 2000 | 89.3 |
| 2 | 1.00 | 50.0 | 30.4 | 30 | 2000 | 75.7 |
| 3 | 4.30 | 204.0 | 141.4 | 90 | 2000 | 97.3 |
| 4 | 1.00 | 50.0 | 33.2 | 30 | 2000 | 100.0 |
| 5 | 1.00 | 51.0 | 43.1 | 30 | 2000 | 76.7 |
| 6 | 6.00 | 306.0 | 180.6 | 150 | 2000 | 85.7 |
| 7 | 6.30 | 326.0 | 182.4 | 140 | 2000 | 75.7 |
| 8 | 6.00 | 400.0 | 190.0 | 150 | 2400 | 82.4 |
| 9 | 1.00 | 50.0 | 30.0 | 30 | 2300 | 75.7 |
| 10 | 15.00 | 750.0 | 310.0 | 350[2] | 430 | 88.0 |

[1] Dow Corning Fluid 200, 35 cSt (Dow Corning Corp. Midland)
[2] Addition of 200 ml at the rate of 10 ml/min followed by 150 ml at the rate of 2 ml/min.
* Copolymer of D,L- lactide and glycolide 50:50

TABLE NO. 2

| Type of measure (unit) | Control * | Compound A encapsulated | Compound A non-encapsulated |
|---|---|---|---|
| Final body weight (g) | 339 + 13 | 342 + 14 | 347 + 28 |
| Ventral portion of prostate (mg) | 337 + 48 | 44 + 6 | 54 + 5 |
| Testicles (g) | 2.81 + 0.13 | 1.15 + 0.08 | 1.36 + 0.14 |
| Tumor* (mg) | 922 + 150 | 186 + 95 | 546 + 0.14 |

TABLE NO. 2-continued

| Type of measure (unit) | Control * | Compound A encapsulated | Compound A non-encapsulated |
|---|---|---|---|
| Increase of tumor volume (%) | 227 + 32 | 106 + 21 | 85 + 19 |

TABLE NO. 3

| Type of measure (unit) | Control * | Compound A encapsulated | Compound A non-encapsulated |
|---|---|---|---|
| Final body weight (g) | 362 + 9 | 363 + 11 | 361 + 11 |
| Ventral portion of prostate (mg) | 419 + 39 | 47 + 5 | 88 + 7 |
| Testicles (g) | 3.14 + 0.07 | 1.26 + 0.06 | 1.83 + 0.07 |
| Tumor* (mg) | 357 + 118 | 68 + 32 | 260 + 68 |
| Increase of tumor volume (%) | 157 + 23 | 81 + 17 | 110 + 28 |

*(Dunning R-3327-H Prostate Carcinoma)

What is claimed is:

1. A sterilized sustained release pharmacological formulation comprising a LH-RH analog and a polylactide-glycolide copolymer having molar proportions of lactide to glycolide of between about 50:50 and 55:45, an average molecular weight of between about 30,000 and 100,000 daltons, and an inherent viscosity of between about 0.5 and 0.8 dl/g when measured in hexafluoroisopropanol (30° C.) at a polymer concentration of about 0.5 g/dl, with between about 20 and 55% of the analog being released the first five days after administration to a human, with the remainder of the analog being released within about 3 weeks to two months thereafter; within said formulation being sterilized by exposure to gamma radiation in such a manner that the properties of the copolymer or formulation are not detrimentally affected.

2. The formulation of claim 1 wherein between about 23 and 50% of the analog is initially released.

3. The formulation of claim 1 wherein the analog is encapsulated by the copolymer.

4. The formulation of claim 1 wherein the analog and copolymer form a matrix compound.

5. The formulation of claim 1 wherein the analog is (pyro)
Glu-His-Trp-Ser-Tyr-D-Trp-Leu-Arg-Pro-Gly-NH$_2$ (pyro)
Glu-His-Trp-Ser-Tyr-D-Phe-Leu-Arg-Pro-Gly-NH$_2$ or (pyro)
Glu-His-Trp-D-Ser-Tyr-D-Leu-Arg-Pro-Gly-NHR[1], where R[1] is an alkyl group.

6. The formulation of claim 1 wherein the stated amount of analog is initially released within three days, with the remainder being released within about 6 weeks.

7. The formulation of claim 1 wherein the stated amount of analog is initially released within one day with the remainder being released within about one month.

8. A sterilized sustained release pharmacological formulation comprising a LH-RH analog which is coated by a copolymer of D,L-lactide and glycolide having molar proportions of lactide to glycolide of between about 50:50 and 55:45, an average molecular weight of between about 30,000 and 100,000 daltons, and an inherent viscosity of between about 0.5 and 0.8 dl/g when measured in hexafluoroisopropanol (30° C.) at a polymer concentration of about 0.5 g/dl, with between about 20 and 55% of the analog being released within the first five days after administration to a human, with the remainder of the analog being released within about 3 weeks to 2 months thereafter, said coated analog being sterilized by exposure to gamma radiation in such a manner that the properties of the coating and/or the analog are not detrimentally affected.

9. The formulation of claim 8 wherein the average molecular weight is between about 36,000 and 50,000 and wherein the inherent viscosity is between 0.5 and 0.7.

10. The formulation of claim 8 wherein the LH-RH anolog is:

(pyro)
   Glu-His-Trp-Ser-Tyr-D-Trp-Leu-Arg-Pro-Gly-NH$_2$, (pyro)
   Glu-His-Trp-Ser-Tyr-D-Phe-Leu-Arg-Pro-Gly-NH$_2$, or (pyro)
   Glu-His-Trp-D-Ser-Tyr-D-Leu-Arg-Pro-Gly-NHR$^1$ wherein R$^1$ is an alkyl group.

11. The formulation of claim 8 wherein the coated compound is obtained as spherical particles having a diameter situated between about 30 and 50 microns.

12. The fomulation of claim 8 wherein the coated compound is obtained as amorphous particles of a size suitable for parenteral injection.

13. The formulation of claim 8 wherein the coated compound amounts to between about 1.7% and 2.9% (in w/w) of the total particles.

14. The formulation of claim 8 wherein the coated compound amounts to between about 1.5% and 3% (in w/w) of the total particles.

15. The formulation of claim 8 wherein the formulation is sterilized by exposure to gamma radiation at a dosage of between about 2.5 and 2.8 Mrad.

16. A process for increasing the paradoxical and antagonistic effect of a LH-RH analog on hormone-dependent diseases in a human, characterized in that a therapeutically effective amount of the pharmacological formulation of claim 1 is administered to said human by injection to increase the paradoxical and antagonistic effect of said analog on said diseases.

17. A process for increasing the paradoxical and antagonistic effect of a LH-RH analog on hormone-dependent diseases in a human, characterized in that a therapeutically effective amount of the pharmacological formulation of claim 8 is administered to said human by injection to increase the paradoxical and antagonistic effect of said analog on said diseases.

18. The process of claim 16 wherein the formulation releases about 23 to 50% of the pharmacologically active compound within 3 days, with the remainder released over a period of up to about 6 weeks.

19. The process of claim 17 wherein the formulation releases about 23 to 50% of the pharmacologically active compound within 3 days, with the remainder released over a period of up to about 6 weeks.

20. The process of claim 16 wherein the formulation releases about 23 to 50% of the pharmacologically active compound within 1 day, with the remainder released over a period between about 25 and 30 days.

21. The process of claim 17 wherein the formulation releases about 23 to 50% of the pharmacologically active compound within 1 day, with the remainder released over a period between about 25 and 30 days.

22. The process of claim 16 wherein the formulation is administered by intramuscular injection.

23. The process of claim 17 wherein the formulation is administered by intramuscular injection.

24. A process for initially stimulating LH and FSH in a human, followed by a suppression of LH and FSH thereafter, which comprises administering by injection to said human a sterilized pharmacological formulation comprising a LH-RH analog and a copolymer of D,L-lactide and glycolide having molar proportions of lactide to glycolide of between about 50:50 and 55:45, an average molecular weight of between about 30,000 and 100,000 daltons, and an inherent viscosity of between about 0.5 and 0.8 dl/g when measured in hexafluoroisopropanol (30° C.) at a polymer concentration of about 0.5 g/dl, which formulation releases between about 20 and 55% of the analog within the first five days after administration by injection for stimulating LH and FSH in said human, followed by suppression of LH and FSH thereafter for a period of at least about 3 weeks to two months.

25. The process of claim 24 wherein the average molecular weight of the copolymer is between 36,000 and 50,000 and the inherent viscosity is between 0.5 and 0.7.

26. The process of claim 24 wherein the formulation is a LH-RH analog of:

(pyro)
   Glu-His-Trp-Ser-Tyr-D-Trp-Leu-Arg-Pro-Gly-NH$_2$, (pyro)
   Glu-His-Trp-Ser-Tyr-D-Phe-Leu-Arg-Pro-Gly-NH$_2$, or (pyro)
   Glu-His-Trp-D-Ser-Tyr-D-Leu-Arg-Pro-Gly-NHR$^1$ wherein R$^1$ is an alkyl group.

27. The process of claim 24 wherein the formulation is sterilized by exposure to gamma radiation at a dosage of between about 2.5 and 2.8 Mrad.

* * * * *

UNITED STATES PATENT AND TRADEMARK OFFICE
CERTIFICATE OF CORRECTION

PATENT NO. : 4,835,139
DATED : May 30, 1989
INVENTOR(S) : Thomas Tice, et al.

It is certified that error appears in the above-identified patent and that said Letters Patent is hereby corrected as shown below:

ON THE TITLE PAGE:

In Abstract, at first line following three indented formulae, "(R' being an alkyl group). On" should read -- (R' being an alkyl group) on --.

In Abstract, at fourth and fifth lines following three indented formulae, change "stimulating effect" to -- release --.

Signed and Sealed this

Twenty-ninth Day of May, 1990

Attest:

HARRY F. MANBECK, JR.

*Attesting Officer*     *Commissioner of Patents and Trademarks*